United States Patent [19]
Harrison et al.

[11] Patent Number: 5,423,751
[45] Date of Patent: Jun. 13, 1995

[54] CONTRAST MEDIA DISPENSING APPARATUS

[76] Inventors: Samuel W. Harrison, 4003 Scenic Dr., Shreveport, La. 71119; John Hardin, III, 948 Trabue, Shreveport

[21] Appl. No.: 19,048
[22] Filed: Feb. 18, 1993
[51] Int. Cl.6 .................................................. A61M 3/00
[52] U.S. Cl. ........................................................... 604/83
[58] Field of Search ................................ 604/251–259, 604/246, 248, 83, 80, 81, 82, 85, 249

[56] References Cited

U.S. PATENT DOCUMENTS

| | | | |
|---|---|---|---|
| 2,866,457 | 12/1958 | Moore | 604/251 |
| 2,999,499 | 9/1961 | Willet | 604/251 |
| 3,001,525 | 9/1961 | Hendricks | 604/251 |
| 3,057,350 | 10/1962 | Cowley | 604/248 |
| 3,533,400 | 10/1970 | Palich | 604/251 |
| 3,776,229 | 12/1973 | McPhee | 604/254 |
| 3,951,145 | 4/1976 | Smith | 604/246 |
| 4,078,563 | 3/1978 | Tuseth | 128/214 |
| 4,175,558 | 11/1979 | Hess, III et al. | 604/254 |
| 4,325,368 | 4/1982 | Kaemmerer | 604/251 |
| 4,425,123 | 1/1984 | DiSalvo | 604/247 |
| 4,428,383 | 1/1984 | DeVroom | 604/248 |
| 4,534,757 | 8/1985 | Geller | 604/246 |
| 4,548,598 | 10/1985 | Theeuwes | 604/251 |
| 4,734,091 | 3/1988 | Boyle et al. | 604/248 |
| 4,750,643 | 6/1988 | Wortrich | 222/81 |
| 4,858,619 | 8/1989 | Toth | 128/748 |
| 4,869,457 | 9/1989 | Ewerlöf | 604/251 |
| 4,892,524 | 1/1990 | Smith | 604/246 |
| 4,976,685 | 12/1990 | Block, Jr. | 604/251 |
| 5,059,173 | 10/1991 | Sacco | 604/80 |
| 5,074,334 | 12/1991 | Onodera | 604/248 |
| 5,078,688 | 1/1992 | Lobodzinski et al. | 604/248 |
| 5,084,031 | 1/1992 | Todd et al. | 604/248 |
| 5,135,026 | 8/1992 | Monska | 604/248 |
| 5,167,643 | 12/1992 | Lynn | 604/251 |
| 5,238,026 | 8/1993 | Goto | 604/246 |

*Primary Examiner*—C. Fred Rosenbaum
*Assistant Examiner*—Manuel Mendez
*Attorney, Agent, or Firm*—John M. Harrison

[57] ABSTRACT

A dispensing system and apparatus for introducing contrast media intravascularly during catheterization procedures, which includes connected segments of tubing that serve as a flow path into the vascular system. A spike is provided at one end of a first segment of the tubing for "spiking" a bottle of contrast media. A stopcock is also provided in the first segment of tubing and a luer lock fitting is attached to the stopcock for connecting a second length of IV (intravascular) tubing fitted with a companion luer lock fitting. In a first preferred embodiment a top check valve is provided in the second segment of tubing, which terminates in the top of a reservoir. A second stopcock is connected to the bottom of the reservoir and a third length of IV tubing projects from the second stopcock and receives a bottom check valve and a second luer lock fitting for securing the bottom end of the third length of IV tubing to a conventional manifold. In alternative embodiments of the invention the top and bottom check valves are omitted from the dispensing system. When the dispensing system is operational, contrast fluid is allowed to flow into the reservoir by manipulating the top stopcock, from which reservoir it flows into the manifold by manipulating the second stopcock and is injected intravascularly into the body from the manifold during the catheterization procedure.

2 Claims, 2 Drawing Sheets

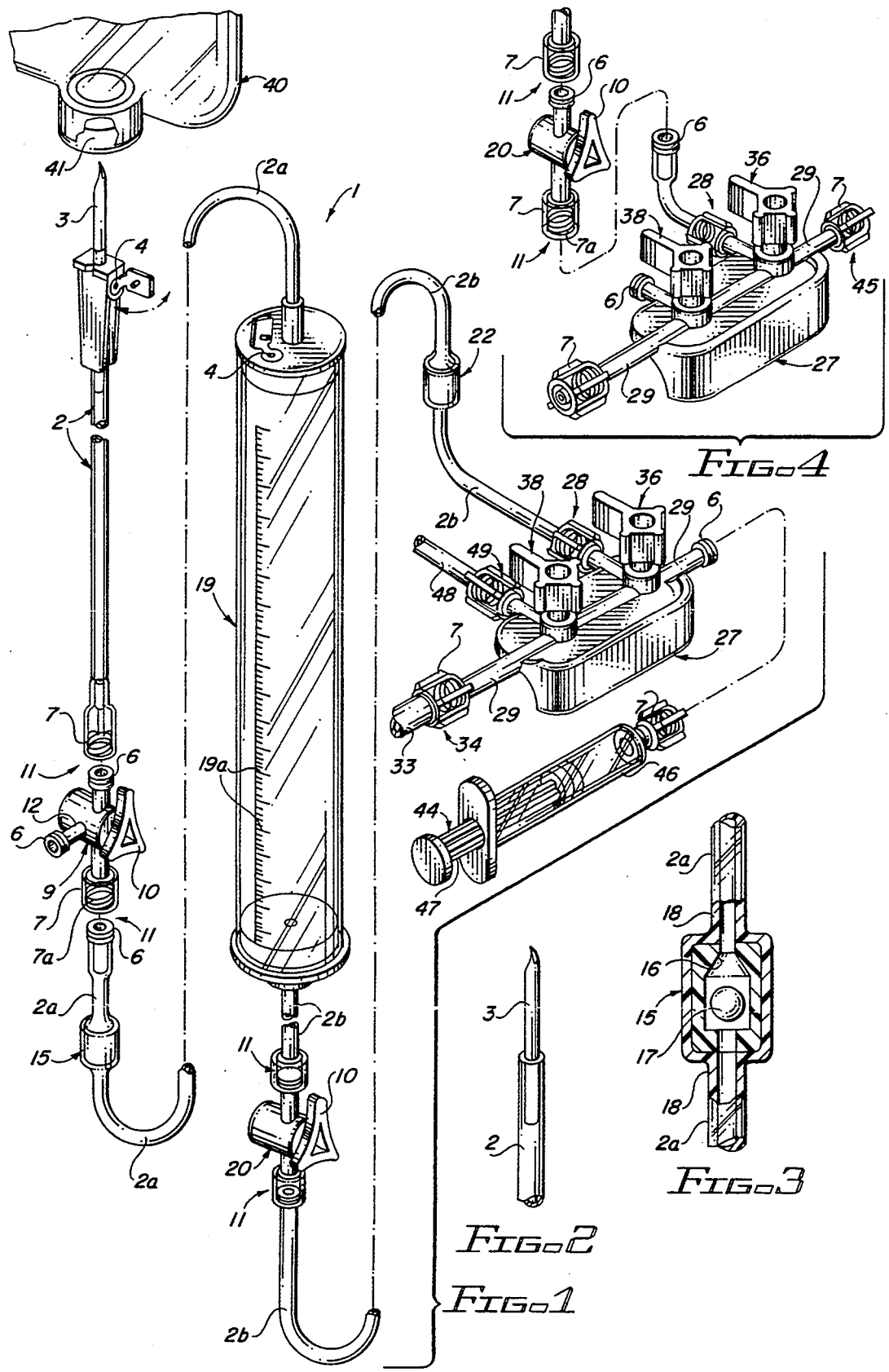

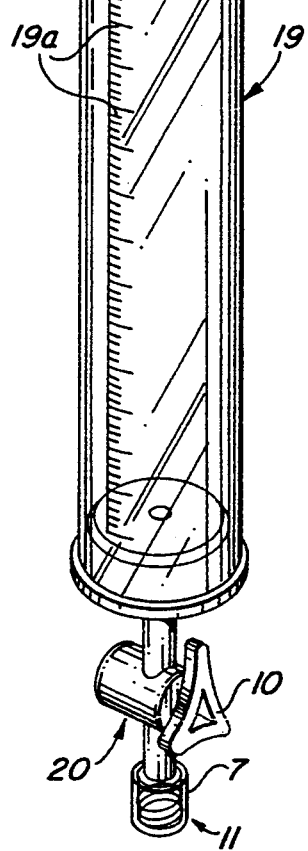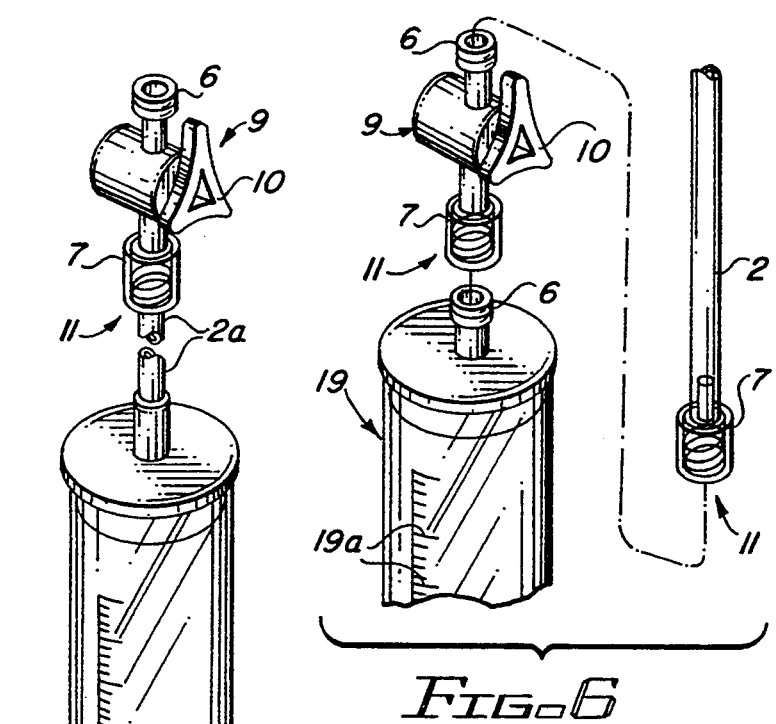

CONTRAST MEDIA DISPENSING APPARATUS

BACKGROUND OF THE INVENTION

1. Field of the Invention

Many techniques and various apparatus for administration of various fluids intravenously into the body for a variety of purposes are well known in the art. Solution administration devices are commonly known as intravascular or "IV" systems and generally include a tubular flow line of selected length having a spike at the upper end which may be inserted into an IV solution bag or bottle and a catheter tip at the opposite end for infusing fluid from the bag or bottle into a patient's vein or artery. The flow line or tube also typically includes a flow regulator in form of a drip chamber and an automated or a thumb-operated device for controlling the rate of fluid flow from the bag or bottle into the flow chamber and to the patient. Variations of this IV system are used during heart catheterization procedures, where a catheter is inserted in a patient's artery or vein, extended into the heart or other area of investigation and a supply of diagnostic radiopaque contrast media is injected from a manifold into the vascular system for angiography in this area. The contrast media is conventionally used for angiography throughout the cardiovascular system, including cerebral and peripheral arteriography, coronary arteriography, ventriculography and the like. Intravascular injection of the radiopaque diagnostic agent contrast media opacifies those vessels in the path of flow of the contrast media, permitting radiographic visualization of the internal structures of the human body. Although the contrast media is particularly well indicated and effective for angiography throughout the cardiovascular system, it is very expensive.

During normal catheterization procedures where contrast media is used, a bottle of contrast media is typically suspended and spiked by one end of a conventional IV apparatus, the opposite end of which is attached to a manifold to facilitate injection of contrast media into the area of investigation at the proper time. Each such procedure requires varying amounts of contrast media and upon completion of each procedure, the IV tubing and unused contrast media, still in the contrast media bottle, are discarded, regardless of the quantity of contrast media remaining in the bottle. This procedure is necessary to avoid the possibility of contamination of the contrast media remaining in the bottle due to pathogens which may reverse-flow by reflux through the IV tubing from the patient into the contrast media. This normal operating technique frequently results in a significant expensive waste for many catheterization procedures, depending upon the quantity of contrast media remaining in the dispensing bottle after the procedure has been completed.

2. Description of the Prior Art

Various types of intravenous systems are well known in the art. U.S. Pat. No. 4,078,563, dated Mar. 14, 1978, to Robert D. Tuseth, details a "Disc Valve In A Container For Dispensing Liquids". The patent describes an improved disc valve in a container for dispensing liquids, which device includes at least two upstanding posts adjacent an outlet passage in the bottom of the container and a floatable disc member with apertures near its periphery, through which the posts extend. The posts are fitted with disc-retaining stops at the upper end. The posts position the disc and the relationship between the size of the apertures and the thickness of the posts assures that the disc will seat over the outlet passage to prevent the passage of air when all the liquid has been dispensed. U.S. Pat. No. 4,425,123, dated Jan. 10, 1984, to F. DiSalvo, details a "Parenteral Liquid Application Apparatus". The apparatus includes a liquid flow control device fitted with a membrane which intermittantly closes and opens flow communication from beneath the dripping tube. A cannula serves to apply the liquid to the patient, the side of the membrane remote from its control side being connected by a capillary tube to the interior of the dripping tube to equalize the pressure changes occurring on both sides of the membrane as the liquid level and supply vessel decreases. The flow rate is initially adjusted by lowering the level of the liquid stabilization device with respect to the level of the dripping chamber. U.S. Pat. No. 4,750,643, dated Jun. 14, 1988, to Theodore S. Wortrich, details a "Sterile Fluid Dispensing System and Method". The system is disposable to enable a succession of individuals to be supplied with a sterile medical solution during operative and other procedures. The system uses a number spaced-apart, penetrable, elastomerically sealed funnels branching from an outlet from the solution container or attached drip chamber. A standard sterile administration set having a spike end may be inserted into the seal of a first funnel to provide flow to a first individual. After the first procedure is completed, the conduit to the first funnel is clamped and the sequence is repeated, but with the spiked end of a second administration set inserted for supply to a second individual. The sequence may be repeated for a selected number of branches. U.S. Pat. No. 4,858,619, dated Aug. 22, 1989, to Marie A. Toth, details an "Intracranial Pressure Monitoring System". The device includes a first valve having a first input port and first and second output ports, with the first output port adapted for connection to a drainage collection bag. A tube connects the input port of the first valve to a patient. A second valve has an input port connected to the second output port of the first valve. A dome member has a first opening for connection with an input port of the second valve, a second opening for receiving a pressure transducer and a third opening to permit balancing of the system. Through this configuration, the drainage collection bag is located before the pressure sensor, but at a maximum distance from the patient to reduce the risk of infection and an automatic relief valve may replace the second valve to provide for automatic venting of dangerously high levels of intracranial fluids. An "Intravenous Administration System" is detailed in U.S. Pat. No. 4,892,524, dated Jan. 9, 1990, to Gordon Smith. The apparatus is designed to administer a volumetric flow of parenteral liquids into a patient's system, through which the quantity of liquid flowing into the system may be easily adjusted. The apparatus includes two separate hydrostatic head pressure systems. The first head pressure is applied from a container, through a metering device with an adjustable fixed orifice to a regulator located a fixed distance below the container. The second head is applied from the regulator, which is designed to prevent air flow through it to the patient. U.S. Pat. No. 5,059,173, dated Oct. 22, 1991, to John J. Sacco, details an IV Apparatus. The IV apparatus includes a gravity flow path fluid for administering IV fluids to a patient, in which multiple IV fluids can be delivered at different flow rates to the patient without having to replace the system apparatus.

It is an object of this invention to provide a contrast media dispensing system or apparatus for dispensing contrast media from a source of supply to a patient, wherein the contrast media unused from a first procedure may be utilized in a second procedure without fear of media contamination during the first procedure.

Another object of this invention is to provide a contrast media dispensing apparatus for safely using substantially all of the contrast media located in a bottle in more than one catheterization procedure, which apparatus includes a spike for spiking a contrast media bottle and a first length of tubing attached to the spike and provided with a stopcock having a luer lock fitting for attachment to a second length of tubing provided with a check valve and terminating in a reservoir. A third length of tubing extends from a second stopcock connected to the reservoir and is fitted with a second check valve and a luer lock fitting for attachment to a conventional manifold. The contrast media may be selectively drained from the bottle into the reservoir during a first catheterization procedure, the entire apparatus below the top stopcock removed and discarded after the first procedure, a second sterile apparatus attached to the in-place first length of tubing and a second catheterization procedure undertaken without contaminating the contrast media remaining in the bottle.

Yet another object of this invention is to provide a contrast media dispensing apparatus for dispensing contrast media from a supply bottle in multiple sequential catheterization procedures without contaminating the remaining contrast media, which apparatus includes a spike for spiking the contrast media bottle, a vent provided in or near the spike, a first length of IV tubing fitted with a stopcock and a luer lock fitting for attachment to a second length of tubing having a check valve and terminating in the top of a reservoir. A third length of IV tubing extends from a second stopcock at the bottom of the reservoir and terminates in another luer lock fitting for attachment to a conventional manifold, wherein the connected second IV tubing, reservoir, second stopcock and third IV tubing may be discarded after the first procedure and a second like apparatus attached to the top stopcock, for using substantially all of the contrast media in the bottle without fear of contaminating the contrast media remaining in the bottle during the first or subsequent procedure.

Still another object of this invention is to provide a contrast media dispensing apparatus for dispensing contrast media from a supply bottle in multiple catheterization procedures without contaminating the contrast media during each procedure, which apparatus includes a vented or unvented spike for spiking the rubber plug in the contrast media bottle and a first length of IV tubing fitted with a stopcock having a luer lock fitting for attachment directly to a reservoir. A third length of IV tubing may be fitted with an optional check valve and extends from a second stopcock connected to the bottom of the reservoir and terminates in a second luer lock fitting for attachment to a conventional manifold, wherein the connected reservoir and third IV tubing may be discarded after the first procedure and a second twin apparatus attached to the top stopcock and the original first length of tubing for using substantially all of the contrast media in the bottle without fear of contaminating the contrast media in the bottle during the first procedure.

SUMMARY OF THE INVENTION

These and other objects of the invention are provided in a contrast media dispensing apparatus for dispensing contrast media from a supply bottle in multiple catheterization procedures without contaminating the contrast media during each procedure, which apparatus includes a vented or unvented spike for spiking the rubber plug in the contrast media bottle, a first length of IV tubing fitted with a stopcock at one end and extending from the spike, a second length of tubing attached to the stopcock and having an optional check valve and terminating in a vented or unvented reservoir and a second stopcock connected to the reservoir and receiving a third length of tubing also optionally fitted with a check valve and adapted for connecting to a conventional manifold.

BRIEF DESCRIPTION OF THE DRAWING

The invention will be better understood by reference to the accompanying drawings, wherein:

FIG. 1 is a perspective exploded view of a first preferred embodiment of the contrast media dispensing apparatus of this invention;

FIG. 2 is an enlarged view of an alternative embodiment of the tubing spike illustrated in FIG. 1;

FIG. 3 is a sectional, enlarged view of a typical check valve provided in the contrast media dispensing apparatus illustrated in FIG. 1;

FIG. 4 is a perspective view of an alternative preferred embodiment of the third length of tubing-to-manifold connection illustrated in FIG. 1;

FIG. 5 is an alternative preferred embodiment of a stopcock-to-manifold connection; and FIG. 6 is an alternative preferred embodiment of a stopcock-to-reservoir connection.

DESCRIPTION OF THE PREFERRED EMBODIMENTS

Referring initially to FIGS. 1-3 of the drawings, in a first embodiment, the contrast media dispensing apparatus of this invention is generally illustrated by reference numeral 1. The dispensing apparatus 1 includes a first length of tubing 2 fitted with a tubing spike 3 for extending through or "spiking" a rubber plug 41, located in the mouth of a contrast media bottle 40. The tubing spike 3 thereby accesses a supply of contrast media located in the contrast media bottle 40, for disposition as hereinafter described. A vent 4 is either built into the tubing spike 3 or may be otherwise provided in the first length of tubing 2 for introducing air into the contrast media bottle 40, for purposes which will be hereinafter described. Alternatively, a non-vented tubing spike 3 may be provided in the top end of the first length of tubing 2, as illustrated in FIG. 2. A top stopcock 9, which may be a 3-way stopcock, is attached to the first length of tubing 2 by means of a first stopcock luer lock 11 and includes a side port 12 and a grip 10 for opening and closing the first length of tubing 2 to facilitate a flow of contrast media from the contrast media bottle 40. A second stopcock luer lock 11 facilitates attachment of the first length of tubing 2 to one end of a second length of tubing 2a, in a first preferred embodiment of the invention. The stopcock luer locks 11 are conventional in design and each include a luer lock flange 6, secured to the top stopcock 9 and second length of tubing 2a, respectively, and a luer lock cap 7 attached to the first length of tubing 2 and the top stopcock 9, respectively.

Each of the luer lock flanges 6 is designed to engage corresponding cap threads 7a, provided in the companion luer lock cap 7, to removably attach the first length of tubing 2 and second length of tubing 2a to the top stopcock 9, for purposes which will also be hereinafter further described. In another preferred embodiment a top check valve 15, a typical design of which is detailed in FIG. 3, is also provided in the second length of tubing 2a to prevent upward, reverse or reflux flow of contrast media through the second length of tubing 2a and first length of tubing 2, and possible contamination of the contrast media, as further hereinafter described. The second length of tubing 2a terminates in the top of a reservoir 19, which is provided with an optional vent 4 and graduations 19a for receiving a selected quantity of contrast media from the contrast media bottle 40 during the catheterization procedure. A bottom stopcock 20 is connected to the bottom of the reservoir 19 by means of a third length of tubing 2b and another stopcock luer lock 11, and a bottom check valve 22, which is identical in design to the top check valve 15, is provided in the third length of tubing 2b, which extends from the bottom stopcock 20 at yet another stopcock luer lock 11. As illustrated in FIG. 3, both the top check valve 15 and bottom check valve 22 may include a pair of nipples 18 for extending into the respective connecting lengths of tubing, a seat 16 and a ball 17, to allow fluid flow from top to bottom by gravity, but serve to block the reflux of contrast media upwardly from bottom to top. A contrast tubing luer lock 28 is provided on the extending end of the third length of tubing 2b and is identical in design to the stopcock luer locks 11. Accordingly, the contrast tubing luer lock 28 is characterized by a luer lock cap 7, fitted with internal cap threads 7a, attached to the extending end of the third length of tubing 2b. The companion luer lock flange 6 is secured to a conventional manifold 27, which is used to inject contrast media intravenously into a patient during the catheterization procedure, according to the knowledge of those skilled in the art. Accordingly, the free end of the third length of tubing 2b is designed to removably connect to the manifold 27 by means of the contrast tubing luer lock 28, as further illustrated in FIG. 1. The manifold 27 is also provided with a like luer lock flange 6, provided in a syringe connecting luer lock 45, to engage the luer lock cap 7 located on the end of a syringe 44. A length of pressure tubing 48 is similarly provided with the luer lock cap 7 element of a pressure tubing luer lock 49 and the luer lock cap 7 is also secured to the manifold 27 by attachment to a corresponding flange of the pressure tubing luer lock 49. In like manner, a catheter luer lock 34 serves to connect a catheter 33 to the corresponding manifold 27 opposite the syringe luer lock 45. A contrast tubing valve 36 is fitted in the manifold 27 and serves to control the flow of contrast fluid from the third length of tubing 2b into the barrel 29 of the manifold 27. A pressure tubing valve 38 is similarly mounted in the manifold 27, in order to control the introduction of pressure through the catheter 33, barrel 29 and pressure tubing 48 from a patient (not illustrated) to a transducer (not illustrated), according to conventional catheterization procedures.

Referring now to FIGS. 4 and 5 of the drawings, it is understood that the reservoir 19 can be connected directly to the manifold 27 by means of the bottom stopcock 20 to eliminate both the bottom check valve 22 and the third length of tubing 2b. Furthermore, as illustrated in FIG. 6, the top check valve 15 and second length of tubing 2a can also be omitted, with the top stopcock 9 connected directly to the reservoir 19, in another alternative embodiment of the invention.

As illustrated in the drawings, under circumstances where it is desirable to use a supply of contrast media stored in a contrast media bottle 40 in a catheterization procedure using the dispensing apparatus 1 illustrated in FIG. 1, the contrast media bottle 40 is initially suspended from a suitable support over a supine patient (not illustrated). The top stopcock 9 is then closed to flow of contrast media and the contrast media bottle 40 is "spiked" by forcing the tubing spike 3 through the rubber plug 41, as illustrated. The first length of tubing 2 which is attached to the tubing spike 3 has been previously connected to the second length of tubing 2a by means of the lower top stopcock luer lock 11. The contrast tubing luer lock 28 is then used to attach the free end of the third length of tubing 2b to the manifold 27 and the dispensing apparatus i is ready for use to selectively dispense contrast media from the contrast media bottle 40, through the connected first length of tubing 2, second length of tubing 2a, reservoir 19 and third length of tubing 2b, into the manifold 27 and catheter 33, to the patient.

A syringe 44 is attached to the manifold 27 using the syringe luer lock 45 and a catheter (not illustrated) is inserted through the catheter 33 into the proper vessel of the patient and the catheter tip located in a selected area of investigation.

A length of pressure tubing 48 is also connected to the manifold 27 by means of the pressure tubing luer lock 49 to receive pulsating pressure from the patient's heart through the catheter 33, the barrel 29 of the manifold 27, into the transducer (not illustrated) to provide the necessary imaging for visual observation of the catheter position in the area of investigation.

Contrast media or fluid is then allowed to flow from the contrast media bottle 40 into the reservoir 19 by opening the top stopcock 9. The contrast media is then supplied to the manifold 27 by opening the bottom stopcock 20 and is selectively introduced into the vessel from the manifold 27 by operation of the syringe 44, to provide a visual radiographic contrast and facilitate clear imaging in the area of investigation.

Referring again to FIGURE 1 of the drawings, if necessary, air can be introduced into the side port 12 of the top stopcock 9 to pressurize the air space in the contrast media bottle 40 and facilitate a more rapid flow of contrast media from the contrast media bottle 90 into the reservoir 19 when the top stopcock 9 is opened. Alternatively, use of either of the vents 4 may provide sufficient pressure equilization to effect this flow of contrast media.

While the present invention has been described with the particularity set forth above, it will be understood that modifications will be apparent to those skilled in the art. Accordingly, the invention is limited only by the following claims.

Having described my invention with the particularity set forth above, what is claimed is:

1. In a contrast fluid dispensing apparatus for dispensing a contrast fluid from a container to a point of contrast fluid distribution and preventing reverse flow of the contrast fluid from the point of contrast fluid distribution to the container, said contrast fluid dispensing apparatus having a first length of tubing connected to the container; a reservoir having one end connected to said first length of tubing; and a second length of tubing having one end connected to the opposite end of the reservoir, with the opposite end of said second length of tubing terminating at said point of contrast fluid distribution, wherein the improvement comprises a first stopcock carried by said first length of tubing for controlling a flow of contrast fluid from the container through said first length of tubing to said reservoir; a luer lock provided on said first stopcock, said luer lock connected to said first length of tubing, for disconnecting said reservoir and said second length of tubing from the container; a first check valve provided in said first length of tubing for preventing a reverse flow of contrast fluid from said reservoir to the container; a second stopcock carried by said second length of tubing, said second stopcock disposed in fluid-communication with said point of contrast fluid distribution for selectively dispensing contrast fluid from said reservoir through said second length of tubing to said point of contrast fluid distribution; and a second check valve provided in said second length of tubing for preventing a reverse flow of contrast fluid from said point of contrast fluid distribution through said second length of tubing to said reservoir.

2. In a contrast fluid dispensing apparatus for dispensing a contrast fluid from a bottle to a manifold and preventing reflux of the contrast fluid from the manifold to the bottle, said contrast fluid dispensing apparatus having a first length of tubing; a spike provided on one end of said first length of tubing for connecting said first length of tubing to the bottle in fluid communication; a reservoir provided on the opposite end of said first length of tubing from said one end for receiving a supply of the contrast fluid from the bottle through said first length of tubing; and a second length of tubing having one end attached to said reservoir, with the opposite end of said second length of tubing attached to the manifold, wherein the improvement comprises a first check valve provided in said first length of tubing for preventing reflux of contrast fluid from said reservoir through said first length of tubing to the bottle; a first stopcock provided in said first length of tubing and attachment means provided on said first stopcock, said attachment means connected to said first length of tubing, for selectively opening said first length of tubing and removing said reservoir and said second length of tubing from said spike; a second stopcock provided in said second length of tubing for controlling a flow of contrast fluid from said reservoir to the manifold; and a second check valve provided in said second length of tubing for preventing reflux of contrast fluid from the manifold to said reservoir.

* * * * *